(12) United States Patent
Mitchell

(10) Patent No.: US 12,280,134 B1
(45) Date of Patent: Apr. 22, 2025

(54) TATTOO INK

(71) Applicant: Nicholas Weil Mitchell, Salt Lake City, UT (US)

(72) Inventor: Nicholas Weil Mitchell, Salt Lake City, UT (US)

(*) Notice: Subject to any disclaimer, the term of this patent is extended or adjusted under 35 U.S.C. 154(b) by 706 days.

(21) Appl. No.: 17/535,488

(22) Filed: Nov. 24, 2021

(51) Int. Cl.
  *A61Q 1/00* (2006.01)
  *A61K 8/81* (2006.01)
  *A61Q 1/02* (2006.01)

(52) U.S. Cl.
  CPC .............. *A61K 8/8129* (2013.01); *A61Q 1/02* (2013.01)

(58) Field of Classification Search
  CPC ................................ A61K 8/8129; A61Q 1/02
  USPC ................... 106/31.01, 31.03, 31.13
  See application file for complete search history.

(56) References Cited

U.S. PATENT DOCUMENTS

| 6,013,122 | A | 1/2000 | Klitzman et al. |
| 7,510,603 | B2 | 3/2009 | Michel |
| 2004/0076696 | A1* | 4/2004 | Lia ........................ A61Q 19/00 424/769 |
| 2015/0196478 | A1* | 7/2015 | Duffy ................... A61K 8/8135 424/401 |
| 2016/0243026 | A1* | 8/2016 | Pathak ................. A61K 31/496 |

FOREIGN PATENT DOCUMENTS

| DE | 102017121900 A1 * | 3/2019 | .......... A61K 31/167 |
| EP | 3103206 A2 | 12/2016 | |
| WO | WO-2006105191 A2 * | 10/2006 | .......... A61K 8/4973 |

OTHER PUBLICATIONS

English Translation (Year: 2017).*
English Translation (Year: 2006).*

* cited by examiner

*Primary Examiner* — James E McDonough
(74) *Attorney, Agent, or Firm* — Paul N. Dunlap; Trendak IP Law LLC

(57) ABSTRACT

A tattoo ink particularly useful for light skin. The tattoo ink includes one or more pigment in a carrier solution. The carrier solution includes polyvinyl alcohol, water, ethanol, and a humectant. The humectant may be glycerin or polypropylene glycol or a blend of thereof. The carrier solution may also include witch hazel extract. The polyvinyl alcohol may have a molecular weight range of 30,000 to 85,000 and be at least 98% hydrolyzed.

11 Claims, No Drawings

TATTOO INK

BACKGROUND OF THE INVENTION

This invention relates generally to a tattoo ink useful for light skin, more particularly to tattoo ink comprising polyvinyl alcohol ("PVA") and one or more pigments.

Tattoo inks are largely unregulated and kept trade secret. Studies have identified dozens of ingredients used in tattoo inks including pigments, and carrier materials. As far as the inventor is aware, it is not known or suggested to use polyvinyl alcohol in tattoo ink.

Patents representative of the art include U.S. Pat. Nos. 7,510,603 B2, 6,013,122, and EP 3,106,206 A2.

SUMMARY OF THE INVENTION

The present invention is directed to tattoo ink particularly useful for light skin. The tattoo ink includes pigment(s) in a carrier solution. The carrier solution includes polyvinyl alcohol, water, ethanol, and a humectant. The humectant may be glycerin or polypropylene glycol or a blend of thereof. The polyvinyl alcohol may have a molecular weight range of 30,000 to 85,000 and be at least 98% hydrolyzed. The carrier solution and ink may include an astringent such as witch hazel.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Tattoo ink for light skin according to embodiments of the invention includes PVA, pigments and various additional ingredients. All ingredients are preferably medical grade, unless otherwise indicated. The ink formulation includes an aqueous carrier solution and pigments. The carrier solution may include PVA, ethanol, water, witch hazel and glycerin. Light skin is believed to correlate with an individual's relative levels of pheomelanin and eumelanin, in particular with low levels of eumelanin. The lighter, skin types are more susceptible to sunburn and UV-exposure. The inventive ink formulations are believed to perform well in such conditions.

In a first embodiment, the PVA may be first dissolved in ethanol to make a PVA-ethanol mixture or solution. For example, the PVA-ethanol mixture may comprise 1 g PVA/5 ml of 100 proof ethanol. The PVA may be chosen from various commercial grades ranging in molecular weight from about 30,000 to about 130,000, preferably from about 30,000 to about 85,000, or from 50,000 to 85,000. Blends of different molecular weight ranges of PVA may be used. PVA is typically made by the suspension polymerization of vinyl acetate to produce poly (vinyl acetate) ("PVAc"), followed by hydrolysis of the PVAc. A high degree of hydrolysis is preferred, for example in the range of 98-100%. PVA is considered to have low toxicity and good biocompatibility. The PVA is believed to advantageously block or absorb UV rays when used in the tattoo ink. The PVA also acts a thickener and dispersing medium to help keep the pigment suspended in the solution. It is also believed that the PVA will result in brighter pigment coloration in the skin, because macrophages may absorb the PVA a low rate therefore making more pigment stay in the skin. The PVA used in experiments mentioned herein was purchased from Acros Organics, a division of Thermo Fisher Scientific.

If necessary, the PVA-ethanol mixture may be heated, for example to a temperature in the range of about 30° C. up to about 70° C. to speed up dissolution, and it may then be strained to remove any gel or undissolved particles.

Glycerin (i.e., glycerol) may then be added to the PVA-ethanol mixture, with stirring. Vegetable glycerin functions as a humectant retaining moisture on the skin, and as a viscosity modifier. Other humectants and/or viscosity modifiers, or blends thereof, may be used, such as propylene glycol. Medical grade glycerin is generally pure, but food grades glycerin with up to 1% water or food grade propylene glycol may be suitable.

If necessary, additional water may be added to the solution. Other optional ingredients may be added, such as other humectants, astringents, viscosity modifiers, preservatives, buffers, pH modifiers, antiseptics, and the like. Optional ingredients may be added either at this stage or later at the same time as or after pigment addition.

An alternate route is to start with a PVA-water mixture, adding glycerin as described above. Ethanol may then be added to the mixture, resulting in the final carrier solution to which the pigment or pigments may be added. The ethanol may be 100 proof (i.e., 50% alcohol and 50% water by volume). Ethanol may be useful as an antiseptic in the tattoo ink, as well as possibly functioning as a vasodilator to enhance penetration of the ink into the skin.

The resulting carrier solution comprises water, ethanol, glycerin, and PVA. The water/ethanol/glycerin volume percentages in the carrier solution may range from 5% to 85% for the water, 3% to 61% for the ethanol, and 2% to 24% for the glycerin. An exemplary carrier solution is 49% water, 49% ethanol, and 2% glycerin by volume. These amounts are based on pure ethanol. Any water present in the ethanol is counted in the water amount.

The amount of PVA in the carrier solution may be in the range of 2.0 g/L to 20.g/L, or from 5 to 15 g/L. An exemplary carrier solution may have about 10.g PVA/L of solution.

The pigment(s) may then be added to the carrier solution and stirred or blended until well-dispersed, mixed or dissolved, for example for 30 to 60 minutes. The amount of pigment depends on the dispersibility or solubility of the pigment. The pigment concentration may range from 40 g/L to 1000 g/L. The solution may then be stored in sterile containers. Any desired pigment may be used, including metallic salts (e.g., oxides, selenides, and sulfides of various metals such as iron, barium, zinc, copper, molybdenum, and titanium), organic pigments (e.g., carbon, azo, diketopyrrolopyrrole, quinacridone, anthraquinone, dioxazine, or quinophthalone dyes), vegetable-based pigments, and plastic based pigments. Solution pH may be adjusted or selected if necessary, depending on the pigment used, as some pigments are pH sensitive.

An exemplary ink was mixed according to the invention. A PVA-ethanol mixture was prepared at a concentration of 1 g PVA/5 mL of 100-proof ethanol, mixing at 70° C., straining, and then cooling to room temperature. The PVA was 98-98.8% hydrolyzed with a molecular weight of 30,000 to 85,000. To the PVA mixture was added 600 mL ethanol, (100 proof), 15 mL propylene glycol (Food grade), and 15 mL of medical grade glycerin, mixing at a temperature of about 30° C. To this carrier solution was added pigment powder at a concentration of 15 g of pigment per 10 mL of carrier solution, i.e., 60% (w/v %). The finished ink was poured into a sterile container.

The ink was tested for stability and intensity of absorbance of desired color. UV absorption spectrophotometer testing confirmed UV absorption and a shelf-life study confirmed stability.

In a second embodiment, the PVA may be first dissolved in ethanol to make a PVA-ethanol mixture or solution as in the first embodiment. The PVA-ethanol mixture may comprise, for example, 1 g PVA/5 ml of 100 proof ethanol. Glycerin (i.e., glycerol) and witch hazel may then be added to the PVA-ethanol mixture, with stirring. The witch hazel may be a typical 1:3 solution, i.e., comprising 25% witch hazel extract and 75% water by volume. Witch hazel may function as an astringent.

The resulting carrier solution comprises water, ethanol, glycerin, witch hazel, and PVA. The water/ethanol/glycerin/witch hazel volume percentages in the carrier solution may range from 5% to 85% for the water, 1% to 15% for the ethanol, 2% to 24% for the glycerin, and 2% to 40% for the witch hazel extract by volume. An exemplary carrier solution according to this second embodiment is 72% water, 24% witch hazel extract, 1% ethanol, and 2% glycerin by volume. Any water that was present in the ethanol or witch hazel is counted in the water amount. The amount of PVA in the carrier solution may be in the range of 2.0 g/L to 20.g/L, or from 5 to 15 g/L. An exemplary carrier solution may have about 10.g PVA/L of solution.

Other ingredients may be optionally added as described above for the first embodiment. The pigments are again added to the carrier solution as for the first embodiment. The mixing steps may again include heating.

Although the present invention and its advantages have been described in detail, it should be understood that various changes, substitutions, and alterations can be made herein without departing from the scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. The invention disclosed herein may suitably be practiced in the absence of any element that is not specifically disclosed herein.

What is claimed is:

1. A tattoo ink comprising polyvinyl alcohol, water, ethanol, a humectant, and a pigment; wherein the polyvinyl alcohol, the water, the ethanol, and the humectant is a carrier solution for the pigment; and wherein the carrier solution comprises from 2.0 g/L to 20.g/L of the polyvinyl alcohol.

2. The tattoo ink of claim 1 wherein the polyvinyl alcohol has a molecular weight range of 30,000 to 85,000.

3. The tattoo ink of claim 2 wherein the polyvinyl alcohol is hydrolyzed at least 98%.

4. The tattoo ink of claim 1 wherein the carrier solution comprises by volume from 5% to 85% water, from 3% to 61% ethanol, and from 2% to 24% humectant.

5. The tattoo ink of claim 4 wherein the humectant comprises glycerin, polypropylene glycol, or a mixture thereof.

6. The tattoo ink of claim 5 wherein the pigment concentration ranges from 2 to 1000 g per L of the carrier solution.

7. The tattoo ink of claim 1 further comprising an astringent.

8. The tattoo ink of claim 7 wherein the astringent comprises witch hazel.

9. The tattoo ink of claim 8 wherein the witch hazel is introduced as a solution of 25% witch hazel extracts and 75% water by volume.

10. The tattoo ink of claim 9 wherein the carrier solution comprises by volume from 5% to 85% water, from 1% to 15% ethanol, from 2% to 40% witch hazel extract, and from 2% to 24% humectant.

11. The tattoo ink of claim 10 wherein the humectant comprises glycerin, polypropylene glycol, or a mixture thereof.

* * * * *

UNITED STATES PATENT AND TRADEMARK OFFICE
CERTIFICATE OF CORRECTION

| | | |
|---|---|---|
| PATENT NO. | : 12,280,134 B1 | Page 1 of 1 |
| APPLICATION NO. | : 17/535488 | |
| DATED | : April 22, 2025 | |
| INVENTOR(S) | : Nicholas Weil Mitchell | |

It is certified that error appears in the above-identified patent and that said Letters Patent is hereby corrected as shown below:

On the Title Page

In Item (71) the Applicant field, the middle name -Well- should read --Weil--.

Signed and Sealed this
Fourteenth Day of October, 2025

John A. Squires
*Director of the United States Patent and Trademark Office*